(12) United States Patent
Borries

(10) Patent No.: US 11,298,236 B2
(45) Date of Patent: Apr. 12, 2022

(54) DEVICES AND METHODS FOR CEMENTING INSERT BEARING LINER INTO ACETABULAR CUP COMPONENT

(71) Applicant: Zimmer, Inc., Warsaw, IN (US)

(72) Inventor: Paul Borries, Columbia City, IN (US)

(73) Assignee: Zimmer, Inc., Warsaw, IN (US)

( * ) Notice: Subject to any disclaimer, the term of this patent is extended or adjusted under 35 U.S.C. 154(b) by 429 days.

(21) Appl. No.: 16/316,580

(22) PCT Filed: May 22, 2017

(86) PCT No.: PCT/US2017/033795
§ 371 (c)(1),
(2) Date: Jan. 9, 2019

(87) PCT Pub. No.: WO2018/013224
PCT Pub. Date: Jan. 18, 2018

(65) Prior Publication Data
US 2020/0179124 A1 Jun. 11, 2020

Related U.S. Application Data

(60) Provisional application No. 62/361,708, filed on Jul. 13, 2016.

(51) Int. Cl.
*A61F 2/34* (2006.01)
*A61F 2/46* (2006.01)
*A61F 2/30* (2006.01)

(52) U.S. Cl.
CPC .............. *A61F 2/34* (2013.01); *A61F 2/4609* (2013.01); *A61F 2/30771* (2013.01);
(Continued)

(58) Field of Classification Search
CPC ..................................... A61F 2/32; A61F 2/34
See application file for complete search history.

(56) References Cited

U.S. PATENT DOCUMENTS 5,571,198 A * 11/1996 Drucker .............. A61F 2/30744
623/22.34
5,702,477 A 12/1997 Capello et al.
(Continued)

FOREIGN PATENT DOCUMENTS

FR 2827504 A1 1/2003
FR 2837092 A1 9/2003
(Continued)

OTHER PUBLICATIONS

"International Application Serial No. PCT/US2017/033795, International Search Report dated Jul. 21, 2017", 6 pgs.
(Continued)

*Primary Examiner* — Jason-Dennis N Stewart
(74) *Attorney, Agent, or Firm* — Schwegman Lundberg & Woessner, P.A.

(57) ABSTRACT

Described is an acetabular assembly comprising: an acetabular cup component (100) having an outer convex surface (104), an inner concave surface (106) defining a cup cavity, and a plurality of openings (116) that extend between the inner concave surface and the outer convex surface and that are configured to accommodate a fastener for attaching the acetabular cup component to an acetabulum of a patient; an insert bearing liner (200) defined by an inner concave surface (202) and an outer convex surface (206), and configured to be located at least partially within die cup cavity of the acetabular cup component; and a plurality of spacers (300) that are configured to be inserted into the plurality of openings in the acetabular cup component from the inner concave surface.

17 Claims, 4 Drawing Sheets

(52) U.S. Cl.
CPC .............. *A61F 2002/30578* (2013.01); *A61F 2002/30784* (2013.01); *A61F 2002/3401* (2013.01); *A61F 2220/0025* (2013.01)

(56) References Cited

U.S. PATENT DOCUMENTS

| | | | | |
|---|---|---|---|---|
| 5,782,929 | A | * | 7/1998 | Sederholm .......... A61F 2/30744 623/22.34 |
| 6,152,962 | A | * | 11/2000 | DeCarlo, Jr. ............. A61F 2/34 623/22.34 |
| 2013/0310945 | A1 | * | 11/2013 | Slone ................. A61F 2/30744 623/22.34 |

FOREIGN PATENT DOCUMENTS

| | | |
|---|---|---|
| WO | WO-2009092910 A2 | 7/2009 |
| WO | WO-2018013224 A1 | 1/2018 |

OTHER PUBLICATIONS

"International Application Serial No. PCT/US2017/033795, Written Opinion dated Jul. 21, 2017", 8 pgs.

"European Application Serial No. 17726508.9, Communication Pursuant to Article 94(3) EPC dated Aug. 3, 2020", 5 pgs.

"European Application Serial No. 17726508.9, Response filed Feb. 12, 2021 to Communication Pursuant to Article 94(3) EPC dated Aug. 3, 2020", 16 pgs.

"European Application Serial No. 17726508.9, Response filed Jun. 29, 2020 to Communication Pursuant to Article 94(3) EPC dated Dec. 19, 2019", 12 pgs.

"European Application Serial No. 17726508.9, Response to Communication Pursuant to Rules 161(1) and 162 EPC filed Sep. 9, 2019", 17 pages.

"European Application Serial No. 17726508.9, Communication Pursuant to Article 94(3) EPC dated Dec. 19, 2019", 5 pages.

* cited by examiner

DEVICES AND METHODS FOR CEMENTING INSERT BEARING LINER INTO ACETABULAR CUP COMPONENT

CLAIM OF PRIORITY

This application is a U.S. National Stage Application under 35 U.S.C. 371 from International Application Serial No. PCT/US2017/033795, filed May 22, 2017, and published as WO 2018/013224 A1, which claims the benefit of U.S. Provisional Patent Application Ser. No. 62/361,708, filed on Jul. 13, 2016, the benefit of priority of each of which is claimed hereby, and each of which is incorporated by reference herein in its entirety.

BACKGROUND

Total hip replacement surgery is commonly performed to alleviate pain and loss of function in injured and diseased hip joints. During this surgery, the articulating surfaces of the hip joint are replaced with prosthetic components. The replacement prosthetic components can include a femoral component having a convex bearing surface and an acetabular cup component having a mating concave bearing surface. The convex bearing surface of the femoral component is configured to rotate in the concave bearing surface of the acetabular cup component in a manner that approximates the rotation of a patient's femoral head in an acetabulum of a hip. Depending upon the material used for the acetabular cup and femoral components, an insert bearing liner can be included in between the two components.

Over time, the prosthetic components from an earlier hip joint replacement can deteriorate in structure and/or function and may need to be repaired or replaced. In some such circumstances, a patient can undergo a revision hip arthroplasty to repair or replace, for example, a compromised or failed acetabular cup component.

OVERVIEW

One treatment option when replacing an acetabular cup component can be to cement a new insert bearing liner into a fixed acetabular cup component, as it retains the existing, fixed acetabular cup component without compromising existing acetabular bone. The inventor has recognized, among other things, that it can be beneficial, during such revision hip arthroplasty, to insert a new insert bearing liner in the fixed acetabular cup component. The inventor has also recognized that fit and stability of the new insert bearing liner in the fixed acetabular cup component are important. Cement can be used to secure the insert bearing liner into the fixed acetabular cup component. In order to optimize stability of the insert bearing liner, the inventor has recognized that a uniform cement layer, or mantle, between the insert bearing liner and the fixed acetabular cup component is desired. The inventor has also recognized that a desired thickness of the cement layer, such as 0.5 mm, for example, can be necessary to stabilize the insert bearing liner.

The present subject matter can help provide a solution to the problems relating to fit and stability of a new insert bearing liner in a fixed acetabular cup component by adding spacers to existing bone screw holes, or other openings, on an inner concave surface of the fixed acetabular cup component, that are not being currently used with bone screws, or other fasteners, to secure the acetabular cup component in the acetabulum. In accordance with the present subject matter, a new insert bearing liner can be chosen that may accommodate the existing, fixed acetabular cup component and the femoral component. Also, the present subject matter contemplates the use of a plurality of spacers to hold the new insert bearing liner at a desired distance from the acetabular cup component while a layer of cement between the two components is introduced and solidified in order to permanently hold the two components in place. In accordance with the present subject matter, a uniform layer of cement can be applied between the acetabular cup component and insert bearing liner so the insert bearing liner can be held in place and the revision hip arthroplasty may be successful.

An acetabular assembly is described that comprises: an acetabular cup component having an outer convex surface, an inner concave surface defining a cup cavity, and a plurality of openings that extend between the inner concave surface and the outer convex surface and that are configured to accommodate a fastener for attaching the acetabular cup component to an acetabulum of a patient; an insert bearing liner defined by an inner concave surface and an outer convex surface, and configured to be located at least partially within the cup cavity of the acetabular cup component; and a plurality of spacers that are configured to be inserted into the plurality of openings in the acetabular cup component from the inner concave surface, wherein the plurality of spacers are configured to be located between the outer convex surface of the insert bearing liner and the inner concave surface of the acetabular cup component in order to define a gap between the outer convex surface of the insert bearing liner and the inner concave surface of the acetabular cup component. Related methods are also described.

This Overview is intended to provide examples of subject matter of the present patent document. It is not intended to provide an exclusive or exhaustive explanation of the invention. The Detailed Description below is included to provide further information about the present inventive devices and the corresponding methods.

BRIEF DESCRIPTION OF THE DRAWINGS

In the drawings, which are not necessarily drawn to scale, like numerals can describe similar components in different views. The drawings illustrate generally, by way of example, but not by way of limitation, various embodiments discussed in the present patent document.

DETAILED DESCRIPTION

Examples according to this disclosure are directed to an acetabular assembly, which can include an acetabular cup component, an insert bearing liner, and a plurality of spacers for inserting into existing bone screw holes, or other openings, on an inner concave surface of the acetabular cup component. The plurality of spacers can be used to hold the insert bearing liner component at a desired distance from the acetabular cup component while a layer of cement can be applied between the two components and solidified in order to permanently hold the two components in place.

For many years now, prostheses have been implanted in the human body to repair or reconstruct all or part of an articulating skeletal joint, such as a hip joint. The hip joint includes the femur and the pelvis, each of which has a surface for articulation against an adjacent articulation surface of the other bone. The femur has a head having a convex, generally spherically contoured articulation surface. The pelvis includes an acetabulum having a concave, generally spherically contoured articulation surface. The articulation surfaces of the femur and the pelvis form a ball-and-socket type joint.

One or both of the articulation surfaces of the hip joint may fail to perform properly, requiring the defective natural articulation surface to be replaced with a prosthetic articulation surface. In an artificial hip joint, a femoral head and a femoral stem can be used to replace the natural head, stem, and articulating surface of the femur, and an acetabular cup can be used to replace the natural socket and articulating surface of the acetabulum of the pelvis. The artificial femoral stem and head may be an integral unitary component or separate modular components designed to be assembled together. The femoral head can articulate directly against the natural acetabulum or the artificial acetabular cup. The acetabular cup can be received and fixed within the acetabulum of a pelvis. The pelvis can be prepared to receive the acetabular cup by reaming a concavity in the acetabular bone. The acetabular cup typically has an outer surface conforming to the concavity reamed in the acetabular bone of the pelvis, and an inner bearing cavity for receiving the head of the femoral component or a healthy femur. The head articulates in the bearing cavity of the acetabular cup.

Figure 1:
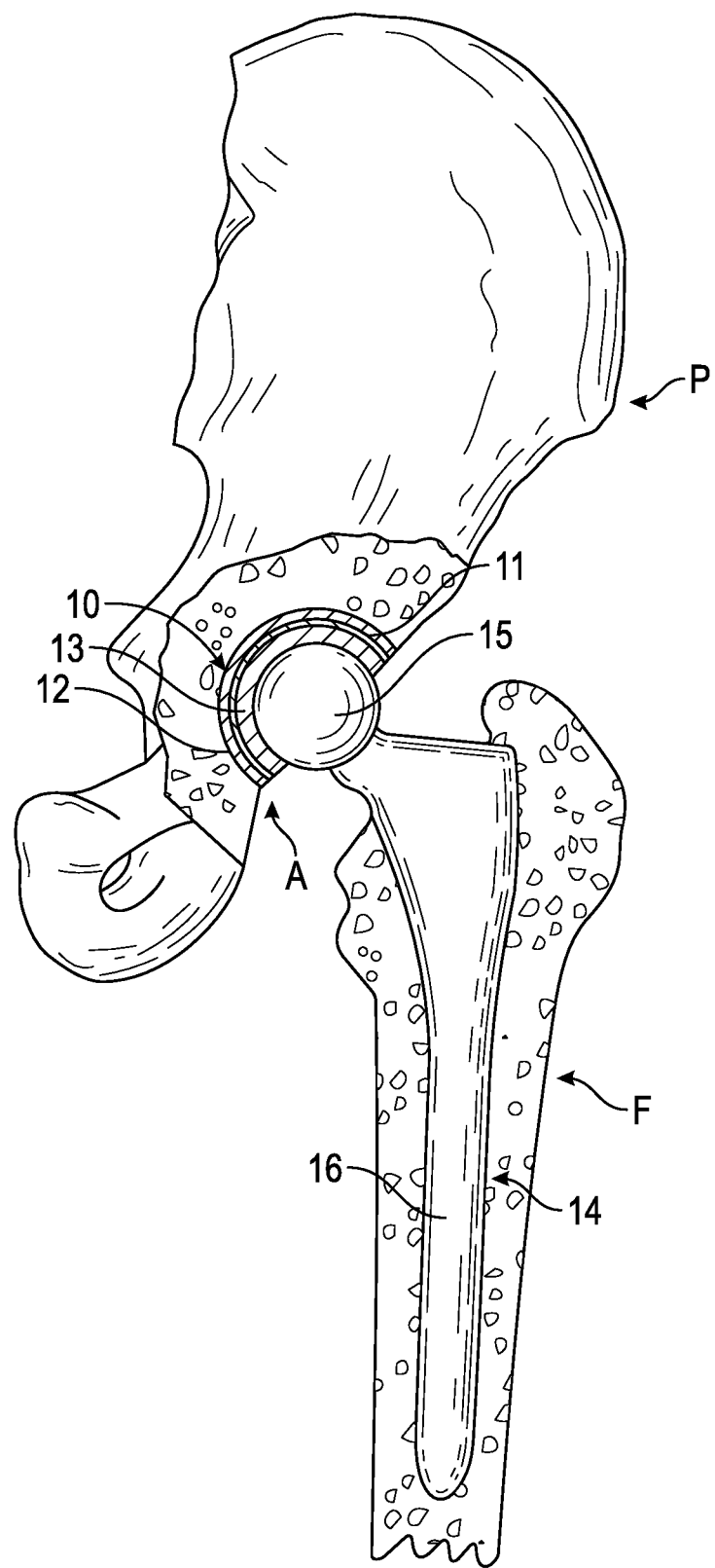
FIG. 1 is a partial sectional view of a hip joint, showing an exemplary prosthetic implant system and surrounding anatomy in accordance with at least one example of the present subject matter.

FIG. 1 depicts an illustrative hip joint prosthesis in accordance with at least one example of the present subject matter. An acetabular assembly 10 is shown placed in a prepared acetabulum "A" of a human pelvis "P". The acetabular assembly 10 can include an acetabular cup component 12 and an insert bearing liner 13 for articulating engagement with a femoral component 14 including a femoral head 15. A cement layer, or mantle, 11 can be located between the acetabular cup component 12 and insert bearing liner 13, in order to attach the two components together. The femoral component 14 can also include a femoral stem 16 that is received within a prepared canal of a proximal femur "F."

Figure 2:
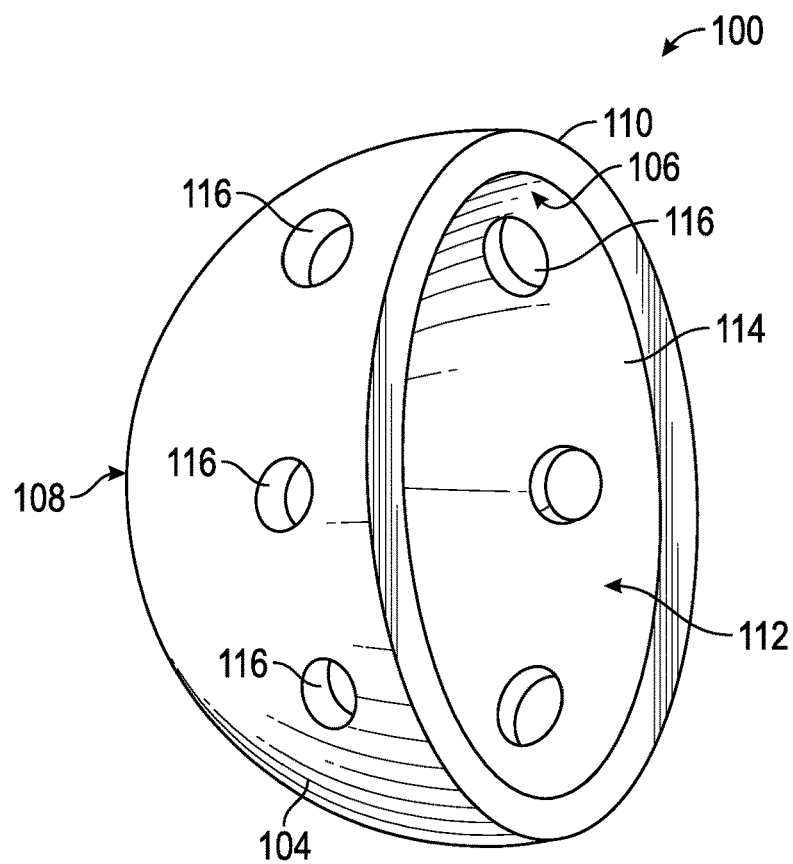
FIG. 2 is a perspective view of an acetabular cup component in accordance with at least one example of the present subject matter.
Figure 3:
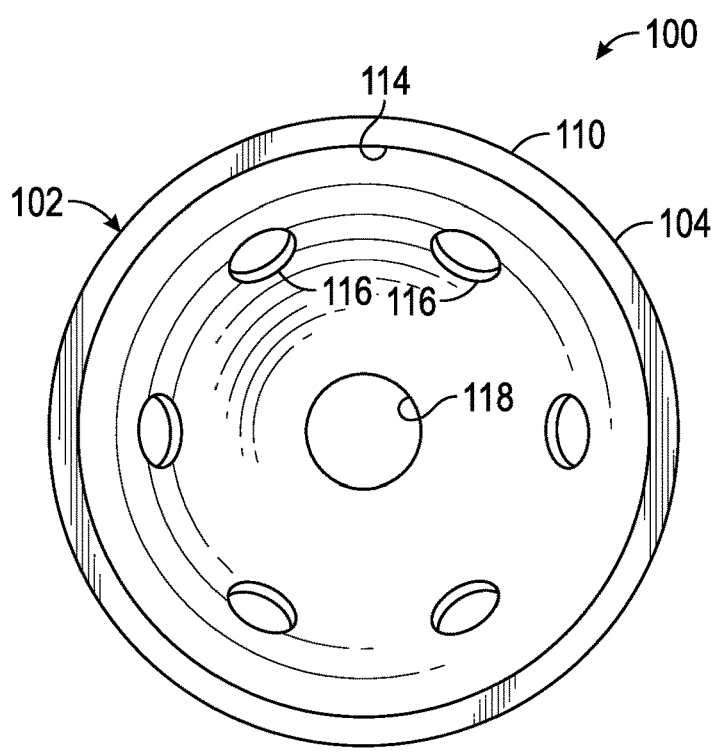
FIG. 3 is a front view of the acetabular cup component of FIG. 2 in accordance with at least one example of the present subject matter.

FIGS. 2 and 3 show an acetabular cup component 100 in accordance with at least one example of the present subject matter. The acetabular cup component 100 can be shaped generally as a hemispherical cup as shown and can have a cup wall 102 comprising an outer convex surface 104 and an inner concave surface 106. The acetabular cup component 100 can have a dome region 108 at the apex of cup wall 102 and an annular rim 110 at the distal end of cup wall 102. The inner concave surface 106 can define a cup cavity 112 having an opening 114 into and through which an insert bearing liner (not shown) can be received.

The acetabular cup component 100 can be formed from a metal alloy such as a titanium alloy (e.g., titanium-6-aluminum-4-vanadium), a cobalt alloy, a stainless steel alloy or a tantalum alloy; a nonresorbable ceramic such as aluminum oxide or zirconia; a nonresorbable polymeric material such as polyethylene; or a nonresorbable composite material such as a carbon fiber-reinforced polymers (e.g., polysulfone).

The outer convex surface 104 of the acetabular cup component 100 can be coated with a porous material, such as a porous metallic material having a network of interconnected pores distributed throughout particles of the metallic material. The particle size of the metallic particles can be chosen to ensure that the resulting interstitial pore size is at least sufficient to permit bone tissue to grow into the porous material for incorporation of the acetabular cup component 100 into the acetabular bone. The metallic particles can be formed from titanium, titanium alloys, cobalt alloys, stainless steel alloys, tantalum alloys, and mixtures thereof. Various methods are known for forming a coating of porous material on the outer convex surface 104. The outer convex surface 104 can also include a textured surface comprising a plurality depressions such as grooves, dimples, or the like. Further, the outer convex surface 104 can also have a coating of a bone ingrowth promoting material such as hydroxyapatite ($Ca_{10}(PO_4)_6OH_2$), a calcium phosphate (e.g., tricalcium phosphate ($Ca_3(PO_4)_2$)), growth factors, bone morphogenic proteins, and mixtures thereof.

The acetabular cup component 100 can be provided with a plurality of openings, through holes, or screw holes 116 which extend through the cup wall 102 in various locations. The inner surface of each opening 116 can be configured to receive and seat a bone screw or other fastener (not shown) of a predetermined shape. It can be seen that the openings 116 can extend completely through the acetabular cup component 100, that is, from the inner concave surface 106 of the acetabular cup component 100 to the outer convex surface 104 of the acetabular cup component 100. The openings 116 can have a diameter greater at the top than at the bottom. Accordingly, the openings 116 may not be cylindrical, but may be tapered or may have a curved inner surface. The openings 116 can have internal threads that are configured to engage threads on a bone screw or other fastener, for example.

If bone screw affixation is used for the acetabular cup component 100, then bone screws can be driven into the acetabular bone through openings 116 in the acetabular cup component 100. Often, the acetabular cup component 100 can be provided with more openings 116 than typically would be used by an implanting physician. This can provide a selection of sites for placement of the bone screws, as can be dictated by the condition of the patient's pelvic bone. Some of the provided openings 116 can receive a bone screw or other fastener while others do not. In an example, all of the openings can receive a bone screw or other fastener.

Referring to FIG. 3, the acetabular cup component 100 can also include a dome hole 118 centered at the apex of dome region 108. The dome hole 118 can be configured to serve as an engagement interface for an instrument (not shown) for holding and positioning the acetabular cup component 100. Typically, such an instrument can be used by the implanting physician to securely grasp the acetabular cup component 100 and place it in a reamed acetabulum. The dome hole 118 can extend completely through the acetabular cup component 100, that is, from the inner surface 106 to the outer surface 104 of the acetabular cup component 100. The dome hole 118 can be an optional feature of the acetabular cup component 100.

Figure 4:
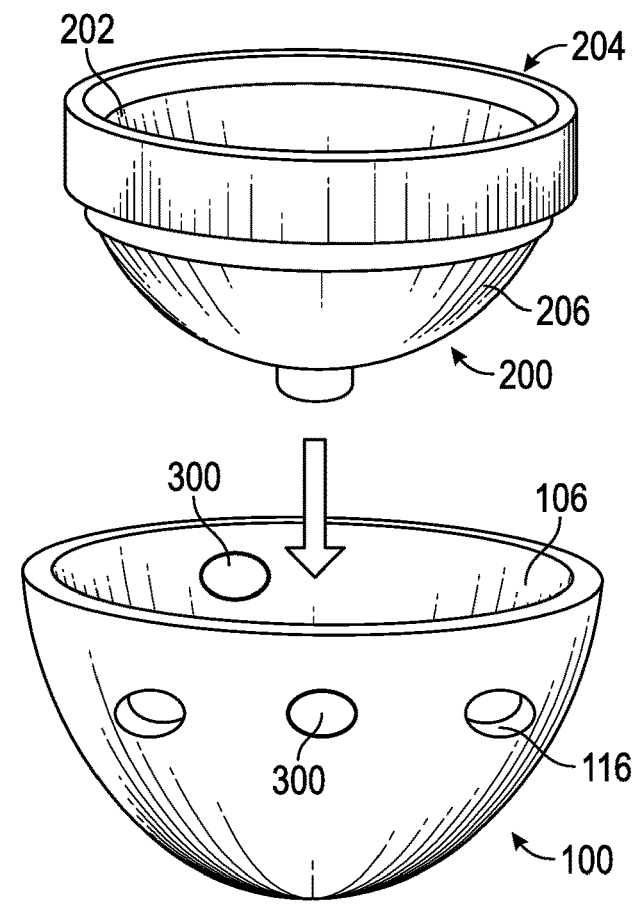
FIG. 4 is an exploded view of an acetabular assembly including an acetabular cup component, an insert bearing liner and spacers in accordance with at least one example of the present subject matter.

FIG. 4 is an exploded view illustrating the acetabular cup component 100 and an insert bearing liner 200 (with no cement layer) in accordance with at least one example of the present subject matter. As depicted by the arrow in FIG. 4, the acetabular cup component 100 can be sized and shaped to receive the insert bearing liner 200. Spacers 300 are shown placed in some of the existing screw holes 116 in the acetabular cup component 100. In various examples, the spacers 300 can be placed in one or more of the existing openings 116 in the acetabular cup component 100 that are not being used to secure the acetabular cup component 100 within the reamed acetabulum.

Proper placement of the insert bearing liner 200 in the acetabular cup component 100 can require a uniform cement layer (not shown) between the two components. If the acetabular cup component 100 is already screwed into bone in a patient's acetabulum, a suitable insert bearing liner, such as 200, can be cemented into the acetabular cup component 100. However, successful attachment of the insert bearing liner 200 and acetabular cup component 100 can require a cement layer that is evenly applied and distributed between the two components. The plurality of spacers 300 can allow a surgeon to choose a suitable insert bearing liner, such as 200, and hold the insert bearing liner 200 a desired distance from the inner surface of the acetabular cup component 100 while a cement layer (not shown) is applied and solidified in order to ensure proper attachment of the insert bearing liner 200 to the acetabular cup component 100.

The insert bearing liner 200 can include a generally hemispherical body having a bearing surface 202, an edge portion 204 extending around the bearing surface 202, and an outer surface 206. The bearing surface 202 can be curved to define a socket space for receiving a femoral head. The outer surface 206 of the inner bearing liner 200 can also be shaped to correspond to the curvature of the inner concave surface 106 of the acetabular cup component 100.

Insert bearing liner 200 can be made of a rigid or a resilient flexible material for withstanding the articulation of a femoral head. The preferred insert bearing liner 200 can be made of ultra-high molecular weight polyethylene and can have a partially spherical bearing cavity that opens distally for receiving a spherical head of a femoral component (not shown) in a ball-and-socket articulating relationship.

The illustrative insert bearing liner 200 and acetabular cup component 100 can be made by a variety of forming processes including machining, casting, forging, compression molding, injection molding, sintering, and/or other suitable processes. The illustrative insert bearing liner 200 and acetabular cup component 100 can be made of a variety of materials including metal, polymer, ceramic, and/or other suitable materials. For example, the insert bearing liner 200 can be made of polyethylene and the acetabular shell 100 from a metal such as cobalt chromium alloy.

A plurality of spacers 300 can be used in the acetabular assembly of FIG. 4. The spacers 300 can be placed or screwed into the openings 116 of the acetabular cup component 100 by a surgeon during surgery. Any suitable number and distribution of spacers 300 can be used in order to provide an even spacing, distance, or gap between the acetabular cup component 100 and the insert bearing liner 200, thus uniformly controlling the thickness of a cement mantle between the two components (not shown).

Spacers 300 can have various shapes and configurations. The shape of the spacers 300 can be generally cylindrically-shaped in order to be seated in a screw hole or other opening in an acetabular cup component. The outer surface of spacers 300 can be dimensionally suited and adapted to substantially contact their mating surfaces of apertures, openings or screw holes 116, for example. The spacers 300 can have an overall height in a range sufficient to fit into any acetabular cup component with screw holes or other such openings. Such a spacer 300 having such a height can be used to allow for an optimum cement layer, or mantle, thickness, such as 1, 2, or 3 millimeters (mm), for example, between the acetabular shell component 100 and the insert bearing liner 200. Other suitable thicknesses of a mantle, or cement layer, are contemplated.

Spacers 300 can be constructed of a biocompatible material, and can be molded of a synthetic resin material that provides a required degree of strength and resilience. The spacers 300 can be made from an acrylic material, such as polymethylacrylate (PMMA), although other materials are also contemplated. Various methods of forming the spacers 300 can be used. The spacers 300 can be formed, for example, by injection molding. However, any suitable method can be used to form a desired shape of the spacers 300. The surface of the spacers 300 can chemically bond with the cement, for example, which can create an interface between the spacers and the cement. PMMA is a primary constituent of currently approved bone cement.

Figure 5:
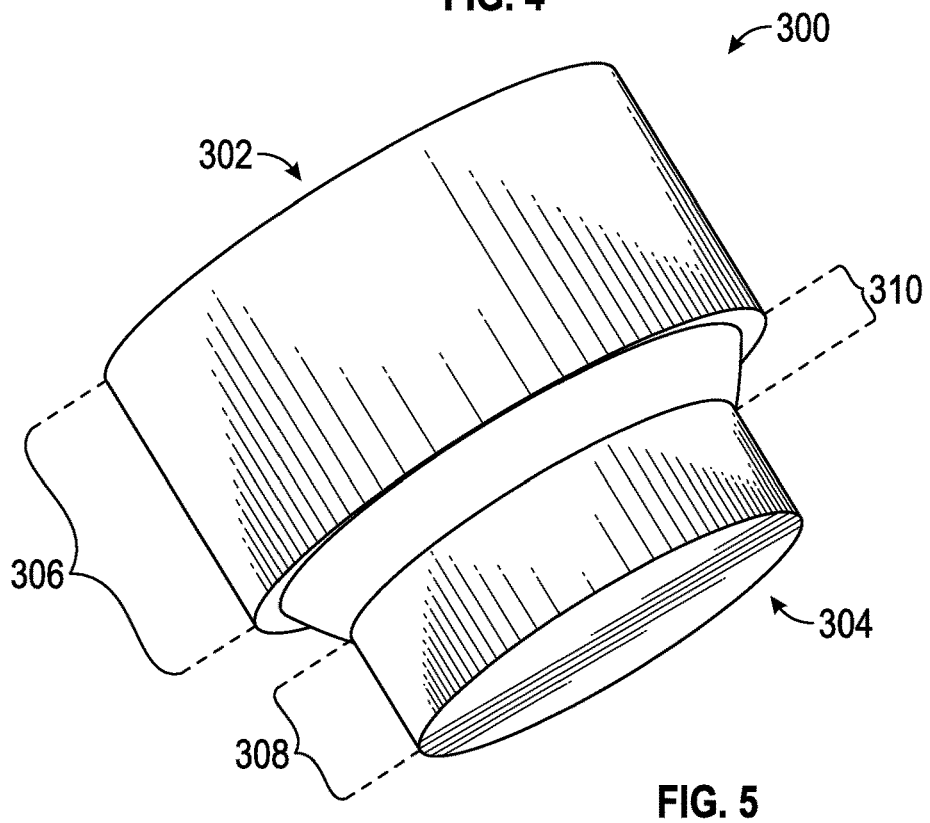
FIG. 5 is a perspective view of a spacer in accordance with at least one example of the present subject matter.

Referring to FIG. 5, a perspective view of an exemplary spacer 300 is shown. Spacer 300 can include a proximal end 302 and a distal end 304. A larger diameter portion 306 can be located adjacent the proximal end 302, and smaller diameter portion 308 can be located adjacent the distal end 304. Both the larger diameter portion 306 and the smaller diameter portion 308 can be generally cylindrically-shaped. A middle section 310 is shown located between the larger diameter portion 306 and the smaller diameter portion 308, and is shown to be frustoconical in shape. The shape of the spacer 300 can be configured such that it can be manually pushed into screw holes in the acetabular cup component from the inner surface side of the acetabular cup component. Such a spacer 300 can form an interference fit with the screw hole, for example. The screw hole, or opening 116, can have a through hole that mates with the smaller diameter portion 308, and a countersink to mate with the middle section 310 of the spacer 300. The size and shape of the larger diameter portion 306 of the spacer 300 can be variable as it can be unconstrained by geometry of the acetabular cup component. Height of the larger diameter portion 306 can be chosen such that the spacer 300 is able to provide a desired or suitable cement mantle thickness. Other shapes and/or configurations of spacers are contemplated, however. Also, other methods of securing the spacers in the screw holes are contemplated. For example, the spacers may be screwed into the openings 116.

Figure 6:
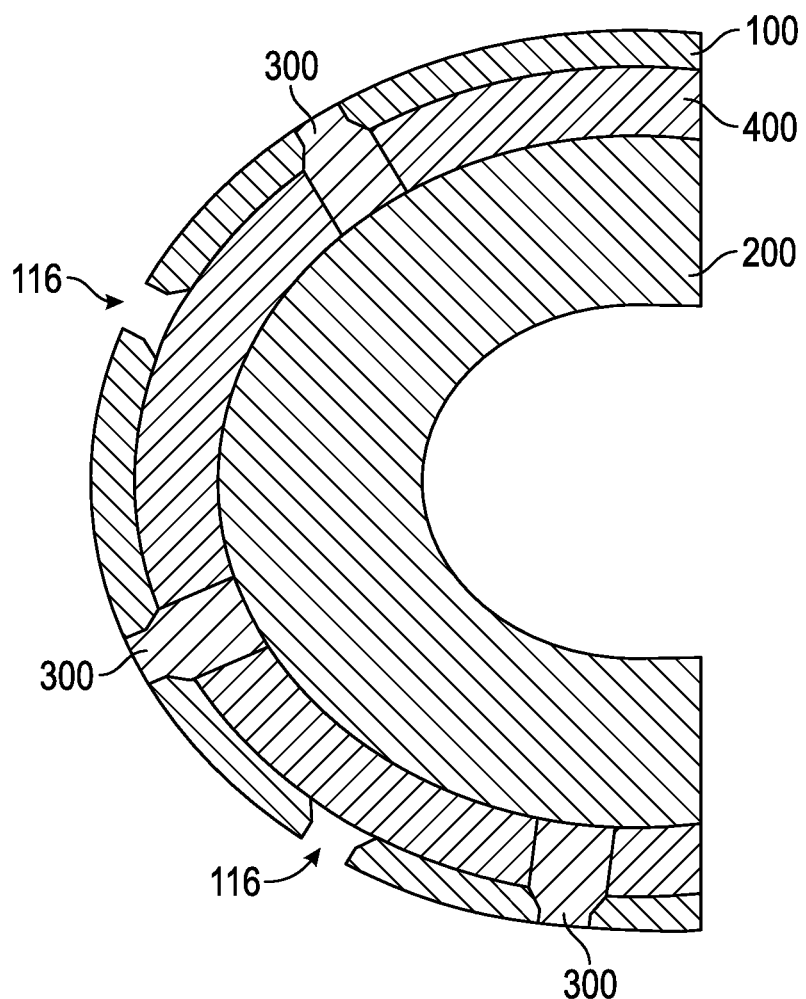
FIG. 6 is a cross-sectional view of an acetabular assembly in accordance with at least one example of the present subject matter.

FIG. 6 is a cross-sectional view of an acetabular assembly in accordance with the invention. Acetabular cup component 100 is shown surrounding insert bearing liner 200. A layer of cement 400 is shown in between the two components. Spacers 300 are shown inserted into some of the plurality of openings 116 in acetabular cup component 100. The figure shows how the spacers 300 abut the insert bearing liner 200 at certain locations in order to allow for a uniform cement layer 400 of a desired thickness to be formed between the acetabular cup component 100 and the insert bearing liner 200.

The cement layer 400 can comprise any number of suitable materials. The cement pre-cursor material, for example, a dough-like substance, can be inserted or injected between the acetabular cup component 100 and the insert bearing liner 200 and surrounding the spacers 300. The cement material can then solidify or cure into cement layer 400. The cement layer 400 can be of a uniform and desired thickness for suitable attachment of the acetabular cup component 100 to the insert bearing liner 200. The thickness of the cement layer 400 can be defined by the thickness or size of the gap between the acetabular cup component 100 and the insert bearing liner 200.

In use, a surgeon can initiate a revision surgery to treat a problematic previously-placed hip implant. In the surgery, the surgeon will commonly make an incision in the patient, and access the previously implanted acetabular cup component. The acetabular cup component can have an outer convex surface, an inner concave surface defining a cup cavity, and a plurality of openings that extend between the inner and outer surfaces and that are configured to accommodate a screw or other fastener for attaching the acetabular cup component to an acetabulum of a patient. After cleaning the acetabular cup component, the surgeon can insert one or more spacers in un-used openings in the inner concave surface of the acetabular cup component. The number and location of the spacers can be chosen to accommodate an insert bearing liner that will be placed within the cup cavity. The insert bearing liner can then be inserted into the cup cavity and placed in contact with the spacers. The outer convex surface of the insert bearing liner can be placed against the plurality of spacers in order to keep a distance between the outer convex surface of the insert bearing liner and the inner concave surface of the acetabular cup component. Cement can then be applied, inserted or injected between the insert bearing liner and the previously implanted acetabular cup component. In this way, a uniform cement layer of a desired thickness can be formed and defined by the gap between the insert bearing liner and acetabular cup component.

Alternatively, the invention can be used with new acetabular cup implantation procedures. The spacers can be placed in screw holes in a new acetabular cup component either before or after the acetabular cup component is screwed into bone in the patient. The remaining steps of the method of implantation and assembly of the acetabular assembly can generally be the same as when an existing, previously-implanted acetabular cup component is used, as in revision surgery.

ADDITIONAL NOTES & EXAMPLES

To better illustrate the method and assemblies disclosed herein, a non-limiting list of embodiments is provided here:

Example 1 includes an acetabular assembly comprising: an acetabular cup component having an outer convex surface, an inner concave surface defining a cup cavity, and a plurality of openings that extend between the inner concave surface and the outer convex surface and that are configured to accommodate a fastener for attaching the acetabular cup component to an acetabulum of a patient; an insert bearing liner defined by an inner concave surface and an outer convex surface, and configured to be located at least partially within the cup cavity of the acetabular cup component; and a plurality of spacers that are configured to be inserted into the plurality of openings in the acetabular cup component from the inner concave surface, wherein the plurality of spacers are configured to be located between the outer convex surface of the insert bearing liner and the inner concave surface of the acetabular cup component in order to define a gap between the outer convex surface of the insert bearing liner and the inner concave surface of the acetabular cup component.

Example 2 includes the acetabular assembly of example 1, further comprising a cement layer formed within the gap between the inner concave surface of the acetabular cup component and the outer convex surface of the insert bearing liner.

Example 3 includes the acetabular assembly of example 2, wherein the cement layer is uniform and has a thickness defined by the gap.

Example 4 includes the acetabular assembly of any one of examples 1-3, wherein the gap between the outer convex surface of the insert bearing liner and the inner concave surface of the acetabular cup component has a uniform width.

Example 5 includes the acetabular assembly of any one of examples 1-4, wherein the plurality of spacers are configured to be secured within the plurality of openings in the acetabular cup component by an interference fit.

Example 6 includes the acetabular assembly of any one of examples 1-5, wherein the plurality of spacers include a larger diameter portion adjacent a proximal end and a smaller diameter portion located adjacent a distal end, and the plurality of spacers are configured to be inserted into the plurality of openings on the acetabular cup component leading with the smaller diameter portion.

Example 7 includes the acetabular assembly of example 6, wherein the larger diameter portion and the smaller diameter portion are cylindrically-shaped.

Example 8 includes the acetabular assembly of any one of examples 6-7, wherein the plurality of spacers includes a middle section located between the larger diameter portion and the smaller diameter portion, and that is frustoconical in shape.

Example 9 includes an acetabular assembly comprising: an acetabular cup component having an outer convex surface, an inner concave surface defining a cup cavity, and a plurality of openings that extend between the inner concave surface and the outer convex surface and that are configured to accommodate a fastener for attaching the acetabular cup component to an acetabulum of a patient; an insert bearing liner defined by an inner concave surface and an outer convex surface, and configured to be located within the cup cavity of the acetabular cup component; a plurality of spacers that are configured to be inserted into the plurality of openings in the acetabular cup component from the inner concave surface, wherein the plurality of spacers are configured to be located between the outer convex surface of the insert bearing liner and the inner concave surface of the acetabular cup component in order to define a gap between the outer convex surface of the insert bearing liner and the inner concave surface of the acetabular cup component; and a cement layer located in the gap between the inner concave surface of the acetabular cup component and the outer convex surface of the insert bearing liner, wherein the cement layer is configured to attach the acetabular cup component and the insert bearing liner.

Example 10 includes the acetabular assembly of example 9, wherein the cement layer is uniform and has a thickness defined by the gap.

Example 11 includes the acetabular assembly of any one of examples 9-10, wherein the plurality of spacers are configured to be inserted and held in place in the plurality of openings in the acetabular cup component by an interference fit.

Example 12 includes the acetabular assembly of any one of examples 9-11, wherein the plurality of spacers include a larger diameter portion adjacent a proximal end and a smaller diameter portion located adjacent a distal end, and the plurality of spacers are configured to be inserted into the plurality of openings on the acetabular cup component leading with the smaller diameter portion.

Example 13 includes the acetabular assembly of example 12, wherein the larger diameter portion and the smaller diameter portion are cylindrically-shaped.

Example 14 includes the acetabular assembly of any of examples 12-13, wherein the plurality of spacers includes a middle section located between the larger diameter portion and the smaller diameter portion, and that is frustoconical in shape.

Example 15 includes a method of assembling an acetabular assembly, comprising: providing or obtaining an acetabular cup component having an outer convex surface, an inner concave surface defining a cup cavity, and a plurality of openings that extend between the inner and outer surfaces and that are configured to accommodate a fastener for attaching the acetabular cup component to an acetabulum of a patient; providing or obtaining a plurality of spacers; inserting the plurality of spacers into the plurality of openings in the acetabular cup component such that the plurality of spacers extend from the inner concave surface; providing or obtaining an insert bearing liner, defined by an inner concave surface and an outer convex surface; placing the insert bearing liner in the cup cavity such that the outer convex surface of the insert bearing liner is placed against the plurality of spacers in order to define a gap between the outer convex surface of the insert bearing liner and the inner concave surface of the acetabular cup component; introducing cement between the inner concave surface of the acetabular cup component and the outer convex surface of the insert bearing liner; and forming a cement layer located in the gap between the inner concave surface of the acetabular cup component and the outer convex surface of the insert bearing liner.

Example 16 includes the method of example 15, wherein the cement layer is uniform and defined by the thickness of the gap.

Example 17 includes the method of any one of examples 15-16, wherein the plurality of spacers are configured to be inserted and held in place in the plurality of openings in the acetabular cup component by an interference fit.

Example 18 includes the method of any one of examples 15-17, wherein the plurality of spacers are inserted into the plurality of openings such that a portion of each of the plurality of spacers extends from the inner concave surface of the acetabular cup component for providing a uniform space between the inner concave surface of the acetabular cup component and the outer convex surface of the insert bearing liner, in order to be filled with cement.

Example 19 includes the method of any one of examples 15-18, wherein the plurality of spacers include a larger diameter portion adjacent a proximal end and a smaller diameter portion located adjacent a distal end, and the plurality of spacers are configured to be inserted into the plurality of openings on the acetabular cup component leading with the smaller diameter portion.

Examples 20 includes the method of any one of examples 15-19, wherein the cement layer is configured to attach the acetabular cup component and the insert bearing liner.

Various examples have been described. These and other examples are within the scope of the following claims.

The above Detailed Description includes references to the accompanying drawings, which form a part of the Detailed Description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, assembly, device, kit, article, or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. An acetabular assembly comprising:
one or more fasteners;
an acetabular cup component having an outer convex surface, an inner concave surface defining a cup cavity, and a plurality of openings that extend between the inner concave surface and the outer convex surface and that are configured to accommodate the one or more fasteners for attaching the acetabular cup component to an acetabulum of a patient;
an insert bearing liner defined by an inner concave surface and an outer convex surface, and configured to be located at least partially within the cup cavity of the acetabular cup component; and
a plurality of spacers that are configured to be inserted into the plurality of openings in the acetabular cup component from the inner concave surface, wherein the plurality of spacers are configured to be located between the outer convex surface of the insert bearing liner and the inner concave surface of the acetabular cup component in order to define a gap between the outer convex surface of the insert bearing liner and the inner concave surface of the acetabular cup component;

wherein the plurality of spacers are configured to be secured within the plurality of openings in the acetabular cup component by an interference fit;

wherein the plurality of spacers each include a larger diameter portion adjacent a proximal end of the spacer, a smaller diameter portion located adjacent a distal end of the spacer, and a middle portion extending from the larger diameter portion to the smaller diameter portion, the plurality of spacers configured to be inserted into the plurality of openings on the acetabular cup component leading with the smaller diameter portion;

wherein the larger diameter portion and the smaller diameter portion are cylindrically-shaped;

wherein the middle portion is frustoconically-shaped; and wherein the distal end of the spacer comprises a planar surface.

2. The acetabular assembly of claim 1, further comprising a cement layer formed within the gap between the inner concave surface of the acetabular cup component and the outer convex surface of the insert bearing liner.

3. The acetabular assembly of claim 2, wherein the cement layer is uniform and has a thickness defined by the gap.

4. The acetabular assembly of claim 1, wherein the gap between the outer convex surface of the insert bearing liner and the inner concave surface of the acetabular cup component has a uniform width.

5. The acetabular assembly of claim 1, wherein the proximal end of the spacer comprises a planar surface.

6. The acetabular assembly of claim 1, wherein the proximal end of the spacer comprises a concave surface.

7. The acetabular assembly of claim 1, wherein the frustoconically-shaped middle portion of the spacer has a constant slope.

8. The acetabular assembly of claim 1, wherein the outer convex surface of the acetabular cup component is coated with a porous material.

9. The acetabular assembly of claim 1, wherein the outer convex surface of the acetabular cup component is coated with a bone ingrowth promoting material.

10. The acetabular assembly of claim 1, wherein the outer convex surface of the acetabular cup component includes a plurality of depressions.

11. The acetabular assembly of claim 10, wherein the depressions comprise grooves.

12. The acetabular assembly of claim 10, wherein the depressions comprise dimples.

13. The acetabular assembly of claim 1, wherein the acetabular cup component includes a dome hole centered at an apex of the acetabular cup component, the dome hole extending from the inner concave surface towards the outer convex surface.

14. The acetabular assembly of claim 13, wherein the dome hole extends completely through the inner concave surface and the outer convex surface of the acetabular cup component.

15. Ari acetabular assembly comprising:

one or more fasteners;

an acetabular cup component having an outer convex surface, an inner concave surface defining a cup cavity, and a plurality of openings that extend between the inner concave surface and the outer convex surface and that are configured to accommodate the one or more fasteners for attaching the acetabular cup component to an acetabulum of a patient;

an insert bearing liner defined by an inner concave surface and an outer convex surface, and configured to be located within the cup cavity of the acetabular cup component;

a plurality of spacers that are configured to be inserted into the plurality of openings in the acetabular cup component from the inner concave surface, wherein the plurality of spacers are configured to be located between the outer convex surface of the insert bearing liner and the inner concave surface of the acetabular cup component in order to define a gap between the outer convex surface of the insert bearing liner and the inner concave surface of the acetabular cup component, and wherein the plurality of spacers are configured to be secured within the plurality of openings in the acetabular cup component by a threaded connection; and a cement layer located in the gap between the inner concave surface of the acetabular cup component and the outer convex surface of the insert bearing liner, wherein the cement layer is configured to attach the acetabular cup component and the insert bearing liner;

wherein the plurality of spacers each include a first cylindrically-shaped portion defined by a first constant diameter, a second cylindrically-shaped portion defined by a second constant diameter, and a middle frustoconically-shaped portion extending from the first cylindrically-shaped portion to the second cylindrically-shaped portion and having a linear slope therebetween, the first constant diameter being larger than the second constant diameter;

wherein the threaded connection is formed between a thread structure on the second cylindrically-shaped portion of the spacer and a complementary thread structure on an internal surface of the opening in the acetabular cup component.

16. The acetabular assembly of claim 15, wherein the cement layer is uniform and has a thickness defined by the gap.

17. The acetabular assembly of claim 15, wherein the plurality of spacers are configured to be inserted into the plurality of openings on the acetabular cup component leading with the second cylindrically-shaped portion.

* * * * *

UNITED STATES PATENT AND TRADEMARK OFFICE
CERTIFICATE OF CORRECTION

| | |
|---|---|
| PATENT NO. | : 11,298,236 B2 |
| APPLICATION NO. | : 16/316580 |
| DATED | : April 12, 2022 |
| INVENTOR(S) | : Paul Borries |

It is certified that error appears in the above-identified patent and that said Letters Patent is hereby corrected as shown below:

On the Title Page

Item (57), in "Abstract", in Column 2, Line 10, delete "die" and insert --the-- therefor In the Claims In Column 12, Line 5, in Claim 15, delete "Ari" and insert --An-- therefor Signed and Sealed this
Seventh Day of June, 2022

Katherine Kelly Vidal
*Director of the United States Patent and Trademark Office*